United States Patent [19]

Aldridge et al.

[11] 4,032,651
[45] June 28, 1977

[54] 3,3a,6,6a-TETRAHYDROFURO[3,4,b]FURAN DERIVATIVES AND ANTI-ULCER COMPOSITION CONTAINING THEM

[75] Inventors: David Cecil Aldridge; Graham Charles Crawley; Colin John Strawson, all of Macclesfield, England

[73] Assignee: Imperial Chemical Industries Limited, London, England

[22] Filed: Sept. 11, 1975

[21] Appl. No.: 612,531

[30] Foreign Application Priority Data

Sept. 27, 1974 United Kingdom ............ 42040/74

[52] U.S. Cl. ........................... 424/279; 260/343.6; 260/485 R; 260/592
[51] Int. Cl.² ..................................... C07D 493/04
[58] Field of Search ............... 260/343.6; 424/285, 424/279

[56] References Cited

UNITED STATES PATENTS 3,930,014  12/1975  Aldridge et al. ................. 424/285

OTHER PUBLICATIONS

Yoshikoshi, Japan Kokai 73–40, 796, Jan. 15, 1973 (cited as C.A. 79:66338d).
Zalinyan, et al., Arm. Khim. Zh. 1973, 26(12) 1015–1019 (cited as C.A. 81:3701n).
Mukaiyama, et al., Bull. Soc. Chem. Jap. 1971, 44(1), 161–166 (cited as C.A. 74:76349u).
Yoshikoshi (II), Japan Kokai 73–40, 797, Jan. 15, 1973 (cited as C.A. 79:66337d).

*Primary Examiner*—Cecilia M. S. Jaisle
*Attorney, Agent, or Firm*—Cushman, Darby & Cushman

[57] ABSTRACT

Pharmaceutical compositions containing 3,3a,6,6a-tetrahydrofuro[3,4-b]furan derivatives including canadensolide and 3-epi-dihydrocanadensolide. Novel 3,3a,6,6a-tetrahydrofuro[3,4-b]furan derivatives bearing a variety of substituents in the 3- and 6-positions selected from alkyl, phenyl, alkoxycarbonyl, methylene, benzylthiomethyl and optionally substituted phenylthiomethyl. The compositions and novel compounds show anti-ulcer activity and are useful in the treatment of gastric or duodenal ulcers.

4 Claims, No Drawings

3,3a,6,6a-TETRAHYDROFURO[3,4-b]FURAN DERIVATIVES AND ANTI-ULCER COMPOSITION CONTAINING THEM

This invention relates to new pharmaceutical compositions which possess ulcer-healing properties.

According to the invention there is provided a pharmaceutical composition which comprises as active ingredient a compound having the formula:

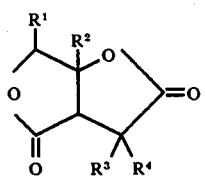

wherein $R^1$ is a hydrogen atom, an alkyl radical of from 1 to 10 carbon atoms or a phenyl radical; $R^2$ is a hydrogen atom or a phenyl radical; and wherein $R^3$ is a hydrogen atom or an alkyl radical of from 1 to 10 carbon atoms and $R^4$ is a hydrogen atom or an alkoxycarbonyl radical of from 2 to 10 carbon atoms; or $R^3$ is a hydrogen atom and $R^4$ is a radical of the formula $R^5SCH_2-$, wherein $R^5$ is a benzyl radical or a phenyl radical optionally bearing one or two substituents selected from halogen atoms, alkyl and alkoxy radicals each of from 1 to 4 carbon atoms, and carboxylic acid radicals; or $R^3$ and $R^4$ together form the methylene ($=CH_2$) radical; but excluding the known optically-active compound dihydrocanadensolide; together with a pharmaceutically-acceptable diluent or carrier.

It will be observed that the furo[3,4-b]furan-2,4-dione structure, which is numbered as follows:

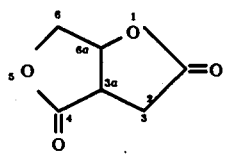

has four potential asymmetric centres, namely those at the 3, 3a, 6 and 6a positions, and that an active ingredient of the composition of the invention may therefore exist in one or more racemic or optically-active forms of varying stereochemistry that is, in varying epimeric forms. It is to be understood that the above definition of active ingredient encompasses any racemic or optionally-active form falling within the said definition which possesses ulcer-healing properties, it being a matter of common general knowledge how such properties may be determined by the tests hereinafter described. It is further to be understood that the two furan rings will always be cis-fused, that is, the hydrogen atom at the 3a-position and the radical $R^2$ at the 6a-position must always be on the same side of the furo[3,4-b]furan nucleus. Throughout this specification the position of the hydrogen atom at the 3a-position and the radical $R^2$ at the 6a-position of the furo[3,4-b]furan will be designated as α-, and the stereochemical arrangement of the other substituents designated α- or β- correspondingly.

Using this nomenclature, the known optically active compound dihydrocanadensolide is the epimer named 6β-n-butyl-3,3aα,6,6aα-tetrahydro-3α-methylfuro[3,4-b]furan-2,4-dione. This configuration for the epimer has been confirmed by Kato et alia, Chemical Communications, (1971), 1561.

A particularly suitable value for $R^1$ or $R^3$ when it is an alkyl radical is, for example, a methyl, ethyl, propyl, butyl, pentyl, hexyl, octyl or decyl radical. A straight-chain alkyl radical is preferred, for example an n-propyl, n-butyl, n-pentyl, n-hexyl, n-octyl or n-decyl radical.

A particularly suitable value for $R^4$ when it is an alkoxycarbonyl radical is such a radical of from 2 to 4 carbon atoms, for example, a methoxycarbonyl or ethoxycarbonyl radical.

A particularly suitable value for an alkyl or alkoxy radical when it is a substituent on the phenyl radical $R^5$ is for example, such a radical of from 1 to 4 carbon atoms, for example a methyl or methoxy radical respectively.

A particularly suitable halogen atom when it is a substituent on the phenyl radical $R^5$ is, for example, a fluorine, chlorine or bromine atom.

A particularly suitable value for $R^5$ is, for example, a 4-fluoro-, 4-chloro-, 4-bromo-, 2-bromo-, 2-methyl-, 3-methyl-, 4-methyl-, 3-methoxy-, 4-methoxy-, 2-carboxy-, or 3-methyl-4-bromo-phenyl radical or a phenyl or benzyl radical.

The pharmaceutical composition of the invention may be obtained by conventional means using conventional diluents and carriers, and it may be in a form suitable for oral administration, for example in the form of a tablet, capsule, aqueous suspension, oily solution or suspension, emulsion, dispersible powder, granule, syrup or elixir; or for parenteral administration, for example in the form of a sterile injectable aqueous suspension or oily solution or suspension; or for rectal administration, as a suppository.

Compositions intended for oral use may be prepared according to any method known to the art for the manufacture of orally-administrable pharmaceutical compositions, and such compositions may contain one or more agents selected from sweetening agents, for example sucrose; flavouring agents, for example essential oils; and colouring agents, in order to provide an elegant and palatable preparation.

The tablets of the invention may contain the active ingredient in admixture with conventional pharmaceutical excipients. Suitable pharmaceutical excipients are, for example, inert diluents, for example lactose; granulating and disintegrating agents, for example calcium carboxymethyl-cellulose, microcrystalline cellulose or maize starch; binding agents, for example polyvinylpyrrolidone; and lubricating agents, for example magnesium stearate. The tablets may be uncoated or they may be coated by known techniques to increase stability or to mask unpalatable taste. They may also be formulated so as to delay disintegration and absorption in the gastro-intestinal tract and thereby provide a sustained action over a longer period.

Formulations for oral use may be presented as hard gelatin capsules containing active ingredient only or containing the active ingredient in admixture with an inert solid diluent, or they may be presented as soft gelatin capsules wherein the active ingredient is mixed with an oily medium.

The aqueous suspensions of the invention may contain the active ingredient in admixture with conventional pharmaceutical excipients. Suitable excipients are, for example, suspending agents, and dispersing or wetting agents.

The pharmaceutical composition of the invention may also be in the form of an oil-in-water emulsion or oily suspension in which the oily phase may be a vegetable or mineral oil, or a mixture of these. A suitable antioxidant or emulsifying agent may also be present.

Dispersible powders and granules suitable for the extemporaneous preparation of an aqueous suspension by the addition of water may contain the active ingredient in admixture with a dispersing or wetting agent, suspending agent and one or more preservatives.

Syrups and elixirs may be formulated with sweetening agents, and may also contain a demulcent, a preservative and flavouring and colouring agents.

Compositions intended for parental administration may sterilised by conventional methods.

The pharmaceutical composition of the invention may alternatively be in the form of a suppository intended for administration of the active ingredient per rectum. Such a composition may be prepared by mixing the active ingredient with a conventional non-irritating excipient which is solid at ordinary temperatures but liquid at the rectal temperature and which will therefore melt in the rectum to release the active ingredients.

The majority of the compounds of formula I are novel compounds. However a specific group of compounds of formula I comprises the known optically active compounds canadensolide and 3-epi-dihydrocanadensolide; the known racemic compounds of formula I wherein $R^1$ is an n-butyl radical, $R^2$ is a hydrogen atom and $R^3$ and $R^4$ are both hydrogen atoms, or $R^3$ and $R^4$ together form the methylene radical, or $R^3$ is a hydrogen atom and $R^4$ is a methoxycarbonyl radical; the known racemic compounds of formula I wherein $R^1$ is a methyl radical, $R^2$ is a phenyl radical, $R^3$ is a hydrogen atom or a methyl radical and $R^4$ is a hydrogen atom; and the known racemic compound 6α-ethyl-3,3aα,6,6aα-tetrahydrofuro[3,4-b]furan-2,4-dione.

Within this specific group, the compounds other than the last three form another specific group, and of these, the known optically active compounds, canadensolide and 3-epi-dihydrocanadensolide are preferred.

The canadensolide used as active ingredient in the composition of the invention may be obtained by fermentation of the organism Penicillium canadense, as described by McCorkindale et alia, Tetrahedron Letters, (1968), 727. Canadensolide is 6β-butyl-3-methylene-3,3aα,-6α,6aα-tetrahydrofuro[3,4-b]furan-2,4-dione.

The 3-epi-dihydrocanadensolide (6β-butyl-3β-methyl-3α,3aα,6α,6aα-tetrahydrofuro[3,4-b]furan-2,4-dione) used as active ingredient in the composition in the composition of the invention has been described by T. P. Roy, Ph.D. Thesis, University of Glasgow, 1970, and it is obtained as a solid of m.p. 70° C., by a conventional catalytic hydrogenation of the 3-methylene group in canadensolide.

The various known racemic compounds used as specific active ingredients in the composition of the invention may be obtained as described by Kato et alia, Chemical Communications, (1971), 1561 and by Mukaiyama et alia, Bulletin of the Chemical Society of Japan, 1971, 44, 101.

According to a further feature of the invention there is provided a novel 3,3a,6,6a-tetrahydrofuro[3,4-b]furan-2,4-dione of the formula:-

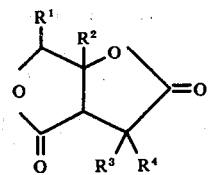

wherein $R^1$ is a hydrogen atom, an alkyl radical of from 1 to 10 carbon atoms or a phenyl radical; $R^2$ is a hydrogen atom or a phenyl radical; and wherein $R^3$ is a hydrogen atom or an alkyl radical of from 1 to 10 carbon atoms and $R^4$ is a hydrogen atom or an alkoxycarbonyl radical of from 2 to 10 carbon atoms; or $R^3$ is a hydrogen atom and $R^4$ is a radical of the formula $R^5SCH_2$-, wherein $R^5$ is a benzyl radical or a phenyl radical optionally bearing one or two substituents selected from halogen atoms, alkyl and alkoxy radicals each of from 1 to 4 carbon atoms, and carboxylic acid radicals; or $R^3$ and $R^4$ together form the methylene radical ($=CH_2$); but excluding such compounds wherein:

a. $R^1$ is an n-butyl radical, $R^2$ is a hydrogen atom, and either $R^3$ is a hydrogen atom and $R^4$ is a hydrogen atom or a methoxycarbonyl radical, or $R^3$ is a methyl radical and $R^4$ is a hydrogen atom, or $R^3$ and $R^4$ together form the methylene radical; or b. $R^1$ is an ethyl radical and $R^2$, $R^3$ and $R^4$ are all hydrogen atoms; or c. $R^1$ is a methyl radical, $R^2$ is a phenyl radical, $R^3$ is a hydrogen atom or a methyl radical, and $R^4$ is a hydrogen atom.

Particular groups of new compounds of the invention comprise those compounds of formula I wherein:

1. $R^1$ is a hydrogen atom, or a methyl, propyl, isopropyl, s-butyl, t-butyl, $C_{5-10}$-alkyl, or a phenyl radical; $R^2$ is a hydrogen atom; and either $R^3$ is a hydrogen atom or $C_{1-10}$-alkyl radical and $R^4$ is hydrogen or a $C_{2-10}$-alkoxycarbonyl radical, or $R^3$ and $R^4$ together form the methylene radical;

2. $R^1$ is a hydrogen atom, a $C_{1-10}$-alkyl, or phenyl radical; $R^2$ is a hydrogen atom; $R^3$ is a $C_{2-10}$-alkyl radical; and $R^4$ is a hydrogen atom or a $C_{2-10}$-alkoxycarbonyl radical;

3. $R^1$ is an ethyl or an n-butyl radical; $R^2$ is a hydrogen atom; $R^3$ is a $C_{2-10}$-alkyl radical; and $R^4$ is a hydrogen atom or a $C_{2-10}$-alkoxycarbonyl radical;

4. $R^1$ is a hydrogen atom, or a methyl, ethyl, propyl, isopropyl, s-butyl, t-butyl or $C_{5-10}$-alkyl radical; $R^2$ is a hydrogen atom; and either $R^3$ is a methyl radical and $R^4$ is a hydrogen atom or a $C_{2-10}$-alkoxycarbonyl radical, or $R^3$ and $R^4$ together form the methylene radical;

5. $R^1$ is a hydrogen atom or a $C_{2-10}$-alkyl radical; $R^2$ is a phenyl radical; $R^3$ is a hydrogen atom or a $C_{1-10}$-alkyl radical; and $R^4$ is a hydrogen atom or a $C_{2-10}$-alkoxycarbonyl radical;

6. $R^1$ is a methyl radical; $R^2$ is a phenyl radical; $R^3$ is a $C_{2-10}$-alkyl radical; and $R^4$ is a hydrogen atom or a $C_{2-10}$-alkoxy carbonyl radical.

A particularly suitable value for $R_1$ or $R_3$, when it is a $C_{2-10}$-alkyl radical is, for example, an ethyl, propyl, butyl, pentyl, hexyl, octyl or decyl radical. A straight-chain alkyl radical is preferred, for example an n-propyl, n-butyl, n-pentyl, n-hexyl, n-octyl or n-decyl radical.

A particularly suitable value for $R_1$ or $R_3$ when it is a $C_{1-10}$-alkyl radical is, for example, a methyl radical or a $C_{2-10}$-alkyl radical as defined immediately above.

A particularly suitable value for $R_1$ when it is a $C_{5-10}$-alkyl radical is for example, a pentyl, hexyl, octyl or decyl radical. A straight-chain alkyl radical is preferred, for example, n-pentyl, n-hexyl, n-octyl or n-decyl radical.

A particularly suitable value for $R_4$ when it is a $C_{2-10}$-alkoxycarbonyl radical is, for example, such a radical of from 2 to 4 carbon atoms, for example, a methoxycarbonyl or ethoxycarbonyl radical.

Another particular group of novel compounds of the invention comprises those compounds of the formula:

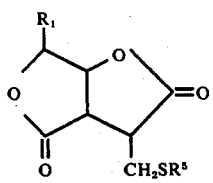
II wherein $R^1$ is a hydrogen atom, an alkyl radical of from 1 to 10 carbon atoms or a phenyl radical, and $R^5$ is a benzyl radical or a phenyl radical optionally bearing one or two substituents selected from halogen atoms, alkyl and alkoxy radicals each of from 1 to 4 carbon atoms, and carboxylic acid radicals.

A particularly suitable value for an alkyl or alkoxy radical when it is a substituent on the phenyl radical $R^5$ is, for example, such a radical of from 1 to 4 carbon atoms, for example, a methyl or methoxy radical respectively.

A particularly suitable halogen atom when it is a substituent on the phenyl radical $R^5$ is, for example, a fluorine, chlorine or bromine atom.

A particularly suitable value for $R^5$ is, for example, a 4-fluoro-, 4-chloro-, 4-bromo-, 2-bromo-, 2-methyl-, 3-methyl-, 4-methyl-, 3-methoxy-, 4-methoxy-, 2-carboxy-, or 3-methyl-4-bromo-phenyl radical or a phenyl or benzyl radical.

Yet further groups of new compounds of the invention comprise those compounds in any one of the above mentioned particular groups wherein $R^1$ has the same configuration as in the naturally occurring compounds canadensolide and dihydrocanadensolide, that is the $\beta$-configuration as defined in this specification.

It will be observed that the majority of novel compounds of the invention are comprised by combinations of the above mentioned particular groups.

According to a further feature of the invention there is provided a novel 3,3a,6,6a-tetrahydrofuro[3,4-b]furan-2,4-dione derivative which is a racemic compound of the formula:

It will be observed that the majority of novel compounds of the invention are comprised by combinations of the above mentioned particular groups.

According to a further feature of the invention there is provided a novel 3,3a,6,6a-tetrahydrofuro[3,4-b]furan-2,4-dione derivative which is a racemic compound of the formula:

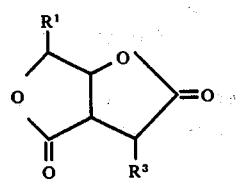
III wherein $R^1$ is an n-butyl radical, and $R^3$ is a methyl radical.

The compound wherein $R^1$ is a $\beta$-n-butyl radical and $R^3$ is a $\beta$-methyl radical is ($\pm$)-3-epi-dihydrocanadensolide, and wherein $R^1$ is a $\beta$-n-butyl radical and $R^3$ is a $\alpha$-methyl radical is ($\pm$)-dihydrocanadensolide, neither of which compounds have been described previously in racemic form.

Specific novel compounds of the invention are set out in Examples 1–19 hereinafter.

The novel compounds of the invention may be obtained by any process applicable to the manufacture of chemically-analogous compounds. Such processes are exemplified by the following in which $R^1$, $R^2$, $R^3$, $R^4$ and $R^5$ have the meanings stated above unless specifically stated otherwise:

a. For a novel compound of formula I wherein $R^4$ is an alkoxycarbonyl radical of from 2 to 10 carbon atoms, that is a compound of the formula:

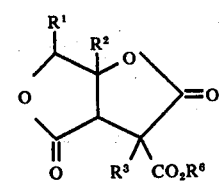
IV wherein $R^6$ is an alkyl radical of from 1 to 9 carbon atoms, oxidising the olefinic bond in a compound of the formula:

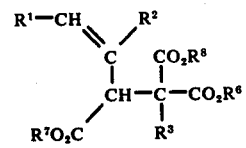
V wherein $R^6$ has the meanings stated above and $R^7$ and $R^8$, which may be the same as or different from $R^6$, are alkyl radicals of from 1 to 9 carbon atoms and cyclising the product thereby obtained by reaction with an acid.

The oxidation is conveniently carried out in a polar organic solvent for example, aqueous acetone or an organic acid, for example formic acid and the cyclisation may optionally be carried out as a separate step in an organic ether, for example, diethyl ether or tetrahydrofuran. Both reactions are conveniently carried out at a temperature of, for example, from 0° C. to 100° C., and particularly at a temperature of from 20° C. to 50° C.

When $R^2$ and $R^3$ are hydrogen atoms the starting material for this process may conveniently be obtained by the reaction of an acetylenic Grignard reagent of the formula $R^1C\equiv C$-Mg-X, wherein X is a halogen atom, for example, a bromine atom, with a compound of the formula:

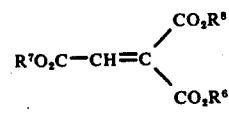
VI wherein $R^6$, $R^7$ and $R^8$ have the meanings stated above, followed by partial hydrogenation of the acetylenic bond in the intermediate thereby obtained which has the structure:

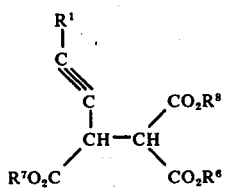

wherein $R^6$, $R^7$ and $R^8$ have the meanings stated above.

When a compound of formula V wherein $R^3$ is an alkyl radical is required, a compound of formula VII or V, wherein $R^3$ is hydrogen, may be alkylated.

The stereochemistry at the 6-position of the furo[3,4-b]furan-2,4-dione nucleus may be determined by the type of oxidation carried out. If a cis-oxidising agent, for example osmium tetroxide, is used, a compound wherein $R^2$ is hydrogen and $R^1$ is other than hydrogen will be obtained in which the hydrogen atoms at the ring-junction positions 3a and 6a and the substituent $R^1$ are all on the same side of the furo[3,4-b]furan nucleus, ($\alpha$-figuration); if a trans-oxidising agent, for example a per-acid, is used, such a compound wherein the three hydrogen atoms at positions 3a, 6 and 6a are all on the same side of the furo[3,4-b]furan nucleus ($\alpha$-configuration) and the substituent $R^1$ is on the opposite side ($\beta$-configuration) will be obtained.

When a cis-oxidising agent for example, osmium tetroxide, is used for the oxidation, the reaction is particularly conveniently carried out in, for example, aqueous acetone and at a temperature of from 20° C. to 25° C., and the cyclisation is conveniently carried out as a separate step using an anhydrous acid, for example anhydrous hydrogen chloride in an organic ether. When a trans-oxidising agent, for example a per-acid for example performic acid, is used, the reaction is particularly conveniently carried out in an excess of an organic acid, for example formic acid, and at a temperature of from 30° C. to 50° C., and under these conditions the cyclisation also takes place.

b. For a novel compound of formula I wherein $R^4$ is hydrogen, the stages of (i) hydrolysing the corresponding compound of formula I wherein $R^4$ is an alkoxycarbonyl radical of from 2 to 10 carbon atoms and then (ii) decarboxylating the intermediate compound of formula I obtained wherein $R^4$ is a carboxylic acid radical.

The hydrolysis and decarboxylation are conveniently carried out in the same reaction vessel, for example by heating the alkoxycarbonyl derivative with a mineral acid, for example aqueous hydrochloric acid, at from 90° C. to 120° C.

c. For a novel compound of formula I wherein $R^3$ and $R^4$ together form the methylene radical, reacting a carboxylic acid of the formula:

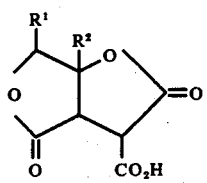

with formaldehyde.

The reaction is conveniently carried out in the presence of an organic acid, for example, acetic acid, a base, for example sodium acetate, and diethylamine.

The reaction is conveniently carried out at a temperature of from 50° C. to 120° C., for example, from 90° C. to 100° C.

The starting material for this process is conveniently obtained in situ by hydrolysing the corresponding ester of formula I wherein $R^4$ is an alkoxycarbonyl radical of from 2 to 10 carbon atoms, by reaction with, for example, a mixture of concentrated hydrochloric acid and acetic acid at a temperature of, for example, from 50° C. to 60° C.

d. For a novel compound of formula I wherein $R^3$ is a methyl radical and $R^4$ is a hydrogen atom, reducing the corresponding compound of formula I wherein $R^3$ and $R^4$ together form the methylene radical.

The reduction may conveniently be carried out in an organic solvent, for example, acetic acid and by means of hydrogen in the presence of a palladium catalyst and at a temperature of, for example, from 0° C. to 30° C. It is to be understood that the hydrogen atom $R^4$ will normally be inserted on the same side of the furo[3,4-b]furan-2,4-dione nucleus as the substituent $R^2$ and the hydrogen atom at position 3a of the nucleus, that is the major product will be the compound of formula I wherein $R^3$ is a $\beta$-methyl radical and $R^4$ is an $\alpha$-hydrogen atom.

e. For a novel compound of formula I wherein $R^2$ and $R^3$ are hydrogen atoms and $R^4$ is a radical of the formula $R^5SCH_2-$, that is a compound of formula II, reacting the corresponding compound of formula I wherein $R^3$ and $R^4$ together form the methylene radical with a thiol of the formula $R^5$-SH.

The reaction is conveniently carried out in a diluent or solvent, for example aqueous tetrahydrofuran, at a temperature of from 0° C. to 40° C., for example at from 20° C. to 25° C., and it is preferably carried out under mild alkaline conditions, for example at about pH 9.

f. For a novel compound of formula I wherein $R^2$, $R^3$ and $R^4$ are each hydrogen, cyclising a comound of the formula:

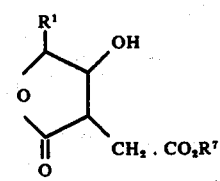

wherein $R^7$ is as defined above.

The cyclisation is conveniently carried out in an anhydrous diluent or solvent, for example ether, in the presence of an acidic reagent, for example dry hydrogen chloride, and at a temperature of, for example, from 0° C. to 100° C., and particularly, at from 20° C. to 50° C.

The starting material of formula IX may be obtained by the catalytic reductin of the corresponding tetronic acid of the formula:-

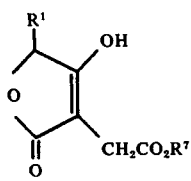

wherein R[7] has the meanings stated above. This tetronic acid may be obtained by conventional means, and the compound wherein R[1] is a hydrogen atom is a known compound.

g. For a novel compound of formula I wherein R[3] is an alkyl radical of from 1 to 10 carbon atoms and R[4] is an alkoxycarbonyl radical of from 2 to 10 carbon atoms, alkylating the corresponding compound of formula I wherein R[3] is a hydrogen atom and R[4] is an alkoxycarbonyl radical of from 2 to 10 carbon atoms by reaction with an alkyl halid of the formula R[9]X, wherein R[9] is an alkyl radical of from 1 to 10 carbon atoms, and X is a displaceable radical, for example, a halogen atom for example, a chlorine, bromine or iodine atom.

The reaction is conveniently carried out in a dry inert diluent or solvent, for example dimethylformamide, at a temperature of, for example, from 40° C. to 100° C., and in the presence of a strong base, for example sodium hydride.

h. For a novel compound of formula I wherein R[2] is a phenyl radical, R[3] is a hydrogen atom or an alkyl radical of from 1 to 10 carbon atoms and R[4] is a hydrogen atom or an alkoxycarbonyl atom of from 2 to 10 carbon atoms, reacting a succinic anhydride derivative of the formula:

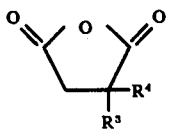

with a reactive intermediate of the formula:-

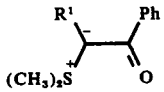

The reaction is conveniently carried out in an inert solvent, for example an organic ether, for example tetrahydrofuran, and at a temperature of, for example, from 20° C. to 100° C., for example at the boiling-point of the solvent.

The intermediate of formula XII used as starting material may be obtained by reacting an α-bromoketone of the formula:

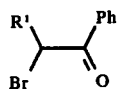

with silver tetrafluoroborate and dimethylsulphide in a solvent, for example acetone, to give a salt of the formula:

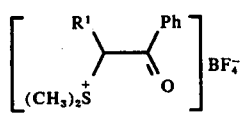

which is then basified with, for example, a mixture of an aqueous solution of sodium hydroxide and an aqueous solution of potassium carbonate, at a temperature of from 0° C. to 20° C.

According to a further feature of the invention there is provided a process for the manufacture of a compound of the formula III wherein R[1] is an n-butyl radical and R[3] is a methyl radical, which comprises the stages of (i) hydrolysing and (ii) decarboxylating the corresponding racemic compound of the formula:-

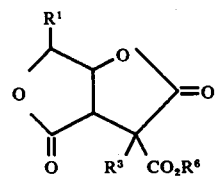

wherein R[1] and R[3] have the meanings stated immediately above and R[6] is an alkyl radical of from 1 to 9 carbon atoms.

The hydrolysis and decarboxylation reactions are conveniently carried out in the same reaction vessel for example by heating the alkoxycarbonyl derivative with a mineral acid, for example hydrochloric acid, in a polar organic solvent, for example acetic acid, at for example from 90° C. to 120° C.

According to a further feature of the invention there is provided a process for the manufacture of a compound of formula III wherein R[1] is an n-butyl radical and R[3] is a methyl radical which comprises reducing racemic canadensolide or 6-epi-canadensolide with hydrogen in the presence of a palladium catalyst, conveniently at a temperature from 0° C. to 30° C. The major product obtained in each case is the compound wherein R[3] is a β-methyl radical.

The compounds of formula I possess ulcer-healing properties and are useful for treating duodenal or gastric ulcers in warm blooded animals.

The ulcer-healing properties may be demonstrated by the oral or subcutaneous administration of the active ingredient to rats in which duodenal ulceration has been produced by the application of acetic acid to the duodenum. In this test the specific compounds of formula I as described in the specification produced a substantial reduction in the size or incidence of duodenal ulcers at a dose in the range from 0.5 mg./kg. to 20 mg./kg. No over toxic effects were detected at the active dose in this test.

The pharmaceutical composition of the invention may contain, in addition to the furo[3,4-b]furan-2,4-dione active ingredient, one or more known drugs known to be of value in the treatment of ulcers and compatible with the furo[3,4-b]furan-2,4-dione derivatives of the invention.

When used for healing ulcers in warm-blooded animals, including humans, it is expected that the active ingredient in the composition of the invention will be administered at a daily dose of between 0.5 and 100 mg. per kg. bodyweight, preferably between 0.5 and 20 mg. per kg. bodyweight, at doses spaced at about 4–5 hourly intervals. A preferable dosage regime in man is a dose of 50 to 200 mg. four times per day.

The invention is illustrated but not limited by the following Examples in which all evaporations are carried out by rotary evaporation under reduced pressure.

EXAMPLE 1

A solution of barium chlorate (0.577 g.) in water (20 ml.) is added to a solution of methyl 2,3-dimethyoxycarbonyloct-cis-4-enoate (0.95 g.) in acetone (22 ml.), osmium tetroxide (0.1 g.) is then added and the mixture is stirred at a temperature of 20°–25° C. for 20 hours, diluted with water, and extracted 3 times with ether (50 ml. each time). The combined ethereal extracts are dried over sodium sulphate, hydrogen sulphide is passed though the solution, and the mixture is filtered. The filtrate is repeatedly treated with hydrogen sulphide and filtered until no further black precipitate is formed, and the final filtrate is again dried over sodium sulphate. Dry hydrogen chloride is passed through the final filtrate, and the mixture is filtered. The solid product is crystallised from a miture of chloroform and petroleum ether (b.p. 60°–80° C.) (hereinafater referred to as petrol") and there is thus obtained in 15% yield, (±)-3,3aα, 6,6aα-tetrahydro-3-methyoxycarbonyl-6α-n-propylfuro-[3,4-b]furan-2,4-dione, m.p. 125°–127° C.

The methyl 2,3-dimethoxycarbonyloct-cis-4-enoate used as starting material is obtained as follows:

Pent-1-yne (26 ml., freshly distilled from anhydrous potassium carbonate) is added dropwise during 30 minutes to a stirred Grignard solution prepared from magnesium (6.3 g.) and ethyl bromide (21 ml.) in tetrahydrofuran (130 ml.) which is heated under reflux, and the mixture is stirred and heated under reflux for a further 15 minutes and then cooled to a temperature of 20°–25° C. Tetrahydrofuran (20 ml.) is added, the mixture is cooled in an ice/salt bath, cuprous chloride (1.6 g.) is added and a solution of methyl 1,3-dimethyoxycarbonylacrylate (35 g.) in tetrahydrofuran (100 ml.) is then added dropwise. The mixture is stirred at 0° C. for 30 minutes, allowed to warm up to a temperature of 20°–25° C. during 50 minutes and then poured into saturated brine (1 litre). The mixture is acidified to pH 2 with concentrated aqueous hydrochloric acid and extracted three times with ether (500 ml. each time). The combined extracts are washed with saturated brine until the washings are no longer acidic, dried (sodium suphate) and evaporated. The residue is distilled under reduced pressure and there is thus obtained in 70% yield, methyl 2,3-dimethoxycarbonyloct-4-ynoate, b.p. 100°–125° C./0.15 mm.

A solution of the above compound (10 g.) in methanol (20 ml.) is added to a mixture of a 5% palladium-on-barium carbonate catalyst (0.6 g.), quinoline (0.24 ml.) and methanol (140 ml.) which has been equilibrated with hydrogen, and the mixture is shaken in an atmosphere of hydrogen at atmosphreic pressure and a temperature of 20°–25° C. until 1.03 litres of hydrogen have been absorbed. The mixture is filtered and the filtrate is evaporated. The residue is dissolved in ether, and the solution is washed with aqueous 3N-hydrochloric acid and then with saturated brine, and then evaporated. There is thus obtained methyl 2,3-dimethyoxycarbonyloct-cis-4-enoate, in 95% yield which is used without further purification.

EXAMPLE 2

The process described in Example 1 is repeated except that oct-1-yne is used in place of pent-1-yne to prepare the starting material. There are thus similarly obtained methyl 2,3-dimethoxycarbonylundec-4-ynoate in ;b 65% yield, b.p. 135°–140° C./0.1 mm.; methyl 2,3-dimethoxy-carbonylundec-cis-1-enoate in 98% yield; and finally (±)-6α-n-hexyl-3,3aα,6,6aα-tetrahydro-3α-methoxycarbonylfuro-[3,4-b]furan-2,4-dione in 19% yield, m.p. 127° C.

EXAMPLE 3

The process described in Example 1 is repeated except that phenylacetylene is used in place of pent-1-yne to prepare the starting material. There are thus similarly obtained methyl 2,3-dimethoxycarbonyl-5-phenylpent-4-ynoate in 57% yield, m.p. 65° C. after crystallisation from ether; methyl 2,3-dimetoxycarbonyl-5-phenylpent-cis-4-enoate in 95% yield; and finally (±)-3,3aα,6,6aα-tetrahydro-3-methoxycarbonyl-6α-phenylfuro[3,4-b]furan-2,4-dione in 24% yield, m.p. 109°–110° C.

EXAMPLE 4

A mixture of (±)-3,3aα,6,6αtetrahydro-3α-methoxycarbonyl-6α-n-propylfuro[3,4-b]furan-2,4-dione (1.2 g.) (Example 1), glacial acetic acid (36 ml.) and aqueous 6N-hydrochloric acid (72 ml.) is heated at 110° C. for 2 hours and then evaporated. The residue is crystallised from a mixture of ether and petrol and there is thus obtained in 82% yield (±)-3,3aα,6,6aα-tetrahydro-6α-n-propylfuro-[3,4-b]furan-2,4-dione, m.p. 92°–93° C.

The process described above is repeated except that the corresponding 6α-n-hexyl derivative (Example 2) of 6α-phenyl derivative (Example 3) is used in place of the 6α-n-propyl derivative. There are thus similarly and respectively obtained in 82% yield, (±)-6α-n-hexyl-3,3aα,6,6aα-tetrahydrofuro[3,4-b]furan-2,4-dione, m.p. 96°14 97° C. and in 87% yield, (±)-3,3aα,6,6aα-tetrahydro-6α-phenylfuro[3,4-b]furan-2,4-dione, m.p. 129°–131° C.

EXAMPLE 5

A solution of (±)-6α-n-butyl-3,3aα,6,6aα-tetrahydro-3-methylenefuro[3,4-b]furan-2,4-dione (0.4 g.) in glacial acitic acid (15 ml.) is added to a suspension of palladous chloride (250 mg.) in glacial acetic acid (5 ml.) which has been equilibrated with hydrogen, and the mixture is shaken in an atmosphere of hydrogen at atmospheric pressure and a temperature of 20°–15° C. until uptake of hydrogen ceases. The mixture is filtered, the filtrate is evaporated, and the residue is crystallised from a mixture of ether and petrol. There is thus obtained in 90% yield, (±)-6α-n-butyl-3,3aα,6,,6aα-tetrahydro-3β-methylfuro-[3,4-b]furan-2,4-dione, m.p. 82°–83° C.

EXAMPLE 6

Thiophenol (0.2 ml.) is added to a solution of canadensolide (0.22 g.) in a mixture of tetrahydrofuran (8 ml.) and aqueous buffer solution of pH 9.2 (1 ml.) and the mixture is kept at a temperature of 20° – 25° C. for 2 hours and then poured into saturated aqueous ammonium chloride solution (50 ml.). The mixture is extracted three times with chloroform (25 ml. each time) and the combined extracts are dried (sodium sulphate) and evaporated. The residue is crystallised from a mixture of chloroform and petrol and there is thus obtained in 46% yield, an epimeric mixture of 6β-n-butyl-3,3aα,6,6aα-tetrahydro-3α- and 6β-n-butyl-3,3aα,6-

,6aα-tetrahydro-3β-phenylthiomethylfuro[3,4-b]furan-2,4-dione, m.p. 108°-110° C.

EXAMPLE 7

A solution of 3-ethoxycarbonylmethyltetronic acid (3-ethoxycarbonylmethyl-2,5-dihydro-4-hydroxyfuran-2-one) (12.6 g.) in glacial acetic acid (40 ml.) is added to a suspension of a 5% rhodium-on-alumina catalyst (3.0 g.) in glacial acetic acid (25 ml.) which has been equilibrated with hydrogen, and the mixture is shaken in an atmosphere of hydrogen at atmospheric pressure and a temperature of 20°-25° C. until 2.5 liters of hydrogen have been absorbed. The mixture is filtered, the filtrate evaporated, and the residue is dissolved in ether. Dry hydrogen chloride is passed through the solution and the solution is cooled to 0° C. and then filtered. The solid product is crystallised from a mixture of acetone and petrol and there is thus obtained in 42% yield, (±)-3,3aα,6,6aα-tetrahydrofuro[3,4-b]furan-2,4-dione, m.p. 125°-127° C.

EXAMPLE 8

The process described in Example 5 is repeated except that racemic canadensolide, (±)-6β-n-butyl-3,3aα,6,6aα-tetrahydro-3-methylenefuro[3,4-b]furan-2,4-dione, is used as starting material. There is thus obtained in 90% yield racemic 3-epi-dihydrocanadensolide, (±)-6β-n-butyl-3,3aα,6,6aα-tetrahydro-3β-methylfuro[3,4-b]furan-2,4-dione, m.p. 74°-76° C.

EXAMPLE 9

The process described in the first part of Example 1 is repeated except that the corresponding olefinic triester of the formula:

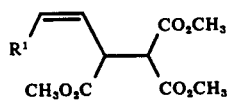

XVI is used in place of methyl 2,3-dimethoxycarbonyloct-cis-4-enoate. There are thus obtained the following (±)-6α-substituted-3,3aα,6,6aα-tetrahydro-3α-methoxycarbonylfuro[3,4-b]furan-2,4-diones:

| Compound No. | 6-substituent | % yield | m.p. (° C.) |
|---|---|---|---|
| 1 | methyl | 23 | 127-129 |
| 2 | n-octyl | 20 | 127-128 |
| 3 | n-decyl | 21 | 128-130 |

The required olefinic triester starting materials of the above formula are obtained using a procedure similar to that described in Example 1 for methyl 2,3-dimethoxycarbonyloct-cis-4-enoate but starting from the corresponding acetylenic triester of the formula:

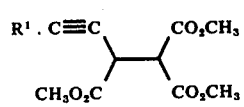

XVII

There are thus obtained methyl 2,3-dimethoxycarbonylhex-cis-4-enoate, methyl 2,3-dimethoxycarbonyltridec-cis-4-enoate and methyl 2,3-dimethoxycarbonylpentadec-cis-4-enoate respectively which are used without purification.

The corresponding acetylenic triester starting materials of the above formula are themselves obtained using a similar procedure to that described for methyl 2,3-dimethoxycarbonyloct-4-ynoate in Example 1 but using the corresponding alk-1-yne in place of pent-1-yne. They have the following properties:

| Ester No. | $R^1$ | Yield % | Physical Properties |
|---|---|---|---|
| 1 | methyl | 36 | b.p. 108-112° C. (0.1 mm.Hg.) m.p. 54-58° C. |
| 2 | n-octyl | 56 | b.p. 152-154° C. (0.1 mm. Hg.) |
| 3 | n-decyl | 66 | b.p. 170-174° C. (0.15 mm. Hg.) |

EXAMPLE 10

A solution of methyl-2,3-dimethoxycarbonylnon-cis-4-enoate (50 g.) in 98% w/v formic acid (150 ml.) is heated at 40° C. with 30% w/v hydrogen peroxide solution (30 ml.) for 3 hours. The solution is cooled and excess peroxides are decomposed by the careful addition of finely divided palladium (0.1 g.) (freshly prepared by reduction of aqueous palladous chloride solution). After filtration, the solution is evaporated to give a gum which is then dissolved in methanol (100 ml.). The solution obtained is saturated with hydrogen chloride during 10 minutes and the mixture evaporated. The residual syrup is dissolved in a 1:4 v/v mixture of ether and petrol respectively and added to a column (7.5 cm., diameter) containing silica gel (2500 g.) in the same solvent. The column is eluted successively with mixtures containing 1:4 v/v (8L.), 3:7 v/v (8L.) and 1:1 v/v (50L.) respectively of ether and petrol. The fractions eluted with the 1:1 v/v mixture of solvents are combined and evaporated. The residue (10 g.) obtained is dissolved in methylene chloride (50 ml.) and evaporated under reduced pressure onto silica gel (50 g.) which has been deactivated with water (12% w/w) and then equilibrated with a 1:50 v/v mixture (10% w/w) of acetone and chloroform. The silica gel residue is added to the top of a dry column (120 cm. × 4.5 cm.) of silica gel (1900 g.) deactivated and equilibrated with solvent as above. The column is then eluted with a 1:50 v/v mixture of acetone and chloroform and fractions (25 ml.) collected and analysed by thin layer chromatography (TLC) on silica gel plates using a 4:95 v/v mixture of acetone and chloroform as eluant (hereinafter referred to as "System A"). There is thus obtained from fractions numbered 80 to 120, after evaporation of solvent and crystallisation of the residue from a mixture of ether and petrol, (±)-6β-n-butyl-3,3aα,6,6aα-tetrahydro-3α-methoxycarbonylfuro[3,4-b]furan-2,4-dione (2.3 g.), m.p. 70°-72° C., $R_f$ 0.63 (System A).

In a similar manner, but starting from the corresponding olefinic triester of formula XVI in Example 9, there are obtained the following (±)-6β-substituted-3,3aα,6,6aα-tetrahydro-3α-methoxycarbonylfuro[3,4-b]furan-2,4-diones:

| Compound No. | 6-substituent | m.p.° C. | Yield % | $R_f$ (System A) |
|---|---|---|---|---|
| 1 | n-hexyl[1] | 70-72 | 4 | 0.69 |
| 2 | methyl[2] | 112-113 | 7 | 0.45 |
| 3 | phenyl[3] | 163-165 | 13 | 0.77 |

Notes:
[1]Initial chromatography in ether / petrol omitted; crude product purified instead by -continued

| Compound No. | 6-substituent | m.p.° C. | Yield % | $R_f$ (System A) |
|---|---|---|---|---| chromatography in chloroform as eluant on a column (120 cm. × 4.5 cm.) of silica gel (1900 g.) loaded dry but deactivated by water (12% w/w) and equilibrated with chloroform (10% w/w); product isolated from fractions (25 ml.) numbered 160 to 190.

[2] Initial chromatography in ether / petrol omitted; crude product purified instead as in Note 1 but using a 1:50 v/v mixture of acetone and chloroform as eluant; product isolated from fractions (25 ml.) numbered 150 to 200.

[3] Product isolated without chromatography by crystallization of crude material from a mixture of acetone and petrol.

EXAMPLE 11

A solution of (±)-6α-n-propyl-3,3aα,6,6aα-tetrahydro-3-α-methoxycarbonylfuro[3,4-b]furan-2,4-dione (1.0 g.) in a mixture of acetic acid (23 ml.), concentrated hydrochloric acid (14 ml.) and water (4 ml.) is stirred at 55° C. for 2 hours to give (±)-6-α-n-propyl-3,3aα,6,6aα-tetrahydrofuro[3,4-b]furan-2,4-dione-3-α-carboxylic acid is situ. Evaporation gave a residue which is shaken for 1 minute at a temperature of 20°-25° C. with a mixture of acetic acid (8 ml.), anhydrous sodium acetate (0.21 g.), 40% w/v aqueous formaldehyde solution (5.8 ml.) and diethylamine (2 ml.). The mixture is heated at 95°-100° C. for 5 minutes and the solution which is obtained is cooled to 20°-25° C., diluted with water (500 ml.) and extracted washed with ether (3 × 100 ml.). The ethereal extracts are washed with saturated aqueous sodium bicarbonate solution, the sodium bicarbonate washings further extracted with ether (50 ml.), and the combined etheral extracts dried (sodium sulphate) and evaporated. The resultant oil crystallises on addition of ether (5 ml.), and is recrystallised from a mixture of ether and petrol to give (±)-6α-n-propyl-3,3aα,6,6aα-tetrahydro-3-methylenefuro[3,4-b]furan-2,4 -dione (0.683 g.), m.p. 60°-63° C.

The above process is repeated using the corresponding (±)-6-substituted-3,3aα,6,6aα-tetrahydro-3-methoxycarbonylfuro[3,4-b]furan-2,4-dione as starting material to give a (±)-6-substituted-3,3aα,6,6aα-tetrahydro-3-methylenefuro[3,4-b]furan-2,4-dione as follows:

| Compound No. | 6-substituent | m.p.° C. | % Yield | Recrystallisation solvent |
|---|---|---|---|---|
| 1 | β-n-hexyl | 90–92 | 56 | ether/petrol |
| 2 | β-phenyl | 159–160 | 65 | ether/petrol |
| 3 | α-methyl | 112–113 | 23 | ether/petrol |
| 4 | α-n-hexyl | 66–67 | 44 | ether/petrol |
| 5 | α-n-octyl | 67–72 | 55 | acetone/petrol |
| 6 | α-n-decyl | 77–78 | 62 | chloroform/petrol |
| 7 | α-phenyl | 134–136 | 44 | chloroform/petrol |

EXAMPLE 12

Using a similar procedure to that described in Example 5 for the preparation of (±)-6α-n-butyl-3,3aα,6,6aα-tetrahydro-3β-methylfuro[3,4-b]furan-2,4-dione, but starting with the corresponding (±)-6-substituted-3,3aα,6,6aα-tetrahydro-3-methylenefuro[3,4-b]furan-2,4-dione as starting material, there are obtained the following (±)-6-substituted-3,3aα,6,6aα-tetrahydro-3β-methylfuro[3,4-b]furan-2,4-dione derivatives:

| Compound No. | 6-substituent | Yield % | m.p.° C. | Recrystallisation solvent |
|---|---|---|---|---|
| 1 | α-n-hexyl | 69 | 100–101 | ether: petrol |
| 2 | α-n-decyl | 81 | 98–99 | ether |
| 3 | α-phenyl | 45 | 164–166 | acetone: petrol |
| 4 | β-n-hexyl | 66 | 55–57 | ether: petrol |

EXAMPLE 13

The proces described in Example 6 is repeated but using the appropriate 6-substituted-3,3aα, 6,6aα-tetrahydro-3-methylenefuro[3,4-b]furan-2,4-dione and substituted mercaptan of the formula $R^5$-SH as starting materials. There is thus obtained a 6-substituted-3,3aα,6,6aα-tetrahydro-3-substituted thiomethylfuro[3,4-b]furan-2,4-dione of the formula:

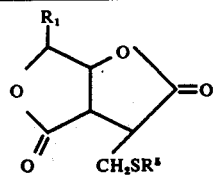

| Compound No. | $R^1$ | $R^5$ | Yield % | m.p.° C. |
|---|---|---|---|---|
| 1 | β-n-butyl | 4-tolyl | 82 | 99–101 |
| 2 | β-n-butyl | 3-tolyl | 49 | 85–86 |
| 3 | β-n-butyl | 2-tolyl | 66 | 105–107 |
| 4 | β-n-butyl | 4-chlorophenyl | 85 | 119–122 |
| 5 | β-n-butyl | 4-bromophenyl | 80 | 110–114 |
| 6 | β-n-butyl | 4-fluorophenyl | 77 | 114–116 |
| 7 | β-n-butyl | 2-bromophenyl | 75 | 104–105 |
| 8 | β-n-butyl | 4-methoxyphenyl | 55 | 68–70 |
| 9 | β-n-butyl | 3-methoxyphenyl | 50 | 79–80 |
| 10 | β-n-butyl | 2-carboxyphenyl | 70 | 124–125 |
| 11 | β-n-butyl | 4-bromo-3-methyl-phenyl | 73 | 102–103 |
| 12 | β-n-butyl | benzyl | 77 | 86–87 |
| 13 | α-n-propyl | phenyl | 61 | 95–97 |
| 14 | α-n-butyl | phenyl | 66 | 98–102 |
| 15 | α-n-octyl | phenyl | 35 | 87–88 |
| 16 | α-n-decyl | phenyl | 65 | 86–87 |
| 17 | α-phenyl | phenyl | 88 | — (see Note 2) |
| 18 | β-n-hexyl | phenyl | 45 | 122–123 |
| 19 | β-phenyl | phenyl | 56 | 199–200 |

Note 1:
These compounds are isolated as epimeric mixtures. Thus compound 1 is a mixture of 6β-n-butyl-3,3aα,6,6aα-tetrahydro-3α- and 6β-n-butyl-3,3aα,6,6aα-tetrahydro-3β-(4-tolyl)thiomethylfuro[3,4-b]furan-2,4-dione.

Note 2:
Compound 17 is isolated as a solid of low melting point but with the following physical properties:-
TLC: single component, $R_f$ 0.69 (System A); $R_f$ 0.26 (on silica plates using a 1:1 v/v mixture of ether and petrol; hereinafter referred to as "System B").
NMR: multiplet, 2.5–2.8τ (10 protons; phenyl-H); singlet, 4.33τ (1 proton, 6β-H); doublet 4.95τ (J 7c/s; 0.8 protons; 6aα-H, epimer 1); doublet, 5.10τ (J6 c/s; 0.2 protons; 6aα-H, epimer 2); multiplet, 6.4–7.0τ (4 protons; 3H, 3aαH and —CH₂S—); 100 MH, spectrum run on sample in solution in deuteriochloroform.

EXAMPLE 14

A solution of an epimeric mixture of 6β-n-butyl3-,3aα,6,6aα-tetrahydro-3α- and 6β-butyl-3,3aα,6,6aα-tetrahydro-3β-phenylthiomethylfuro[3,4-b]furan-2,4-dione (0.1 g.) in chloroform (1 ml.) is injected onto a column of silica gel (60μ particle size; column dimensions 31 × 2.5 cm.) arranged for high pressure liquid chromatography (HPLC). The column is eluted with a 2:3 v/v mixture of methylene chloride and hexane (mixed fraction, b.p. 68°-70° C; hereinafter referred to as "hexane") at a flow rate of 5 ml./min. and the eluant collected in fractions (25 ml.) for analysis by TLC (on silica gel plates, using methylene chloride as eluant). The fractions numbered 31 to 50 are combined and evaporated. The residue obtained is recrystallised from a mixture of chloroform and petrol to give 6β-n-butyl-3,3aα,6,6aα-tetrahydro-3-β-phenylthiomethyl-furo[3,4-b]furan-2,4-dione (0.060 g.), m.p. 118° C., $R_f$ 0.71 (on silica gel using methylenechloride as an eluant). Similarly from fractions numbered 55 to 77 there is obtained, after recrystallisation from a mixture of chloroform and petrol, 6β-n-butyl-3,3aα,6,6aα-tetrahydro-3-α-phenylthio-methylfuro[3,4-b]furan-2,4-dione (0.020 g.), m.p. 127°–128° C., $R_f$ 0.59 (on silica gel using methylene chloride as eluant).

EXAMPLE 15

A solution of (±)-6α-n-butyl-3,3aα, 6,6aα-tetrahydro-3α-methoxycarbonylfuro[3,4-b]furan-2,4-dione (0.512 g.) in dimethylformamide (10 ml., dried by distillation from calcium hydride) is added to a stirred suspension of sodium hydride (0.090 g.) in the same solvent (10 ml.) under an argon atmosphere. Iodomethane (2 ml.) is added and the mixture is heated at 40° C. for 2.5 hours under reflux. After cooling to 20°–25° C., the mixture is added to a saturated aqueous solution of ammonium chloride (500 ml.). The mixture is extracted with chloroform (3 × 100 ml.) and the combined extracts are dried (sodium sulphate) and evaporated under reduced pressure. The residue (0.466 g.) thus obtained is dissolved in methylene chloride (5 ml.) and adsorbed by evaporation of solvent onto silica gel (2.5 g.) which has been deactivated by water (12% w/w) and equilibrated with a 1:33:66 v/v mixture (10% w/w) of acetone, chloroform and petrol respectively. The silica gel residue is added to the top of a dry column (45 × 2.5 cm.) of silica gel (650 g.) prepared as above, and the column eluted with the above three component solvent mixture. Fractions (25 ml.) are then collected and analysed by TLC (System A). The fractions containing material of $R_f$ 0.8 are combined and evaporated under reduced pressure. The residue produced is recrystallised from a mixture of ether and petrol to give the high $R_f$ value, C3-epimer of (±)-6α-n-butyl-3,3aα-tetrahydro-3-methoxycarbonyl-3-methylfuro[3,4-b]furan-2,4-dione (0.085 g.), m.p. 78° C. By a similar treatment of the fractions containing material of $R_f$ value 0.75, there is obtained the lower $R_f$ value, C3-epimer of (±)-6α-n-butyl-3,3aα,6,6aα-tetrahydro-3-methoxycarbonyl-3-methylfuro[3,4-b]furan-2,4-dione (0.097 g.), m.p. 58° C.

Using a similar procedure, there is obtained in 60% yield from (±)-6β-n-butyl-3,3aα,6,6aα-tetrahydro-3α-methoxycarbonylfuro[3,4-b]furan-2,4-dione, a C3-epimeric mixture of (±)-6β-n-butyl-3,3aα,6,6aα-tetrahydro-3-methoxycarbonyl-3-methylfuro[3,4-b]furan-2,4-dione, m.p. 77°–79° C., $R_f$ values: 0.70, 0.50 (System A).

EXAMPLE 16

A solution of (±)-6α-n-butyl-3,3aα,6,6aα-tetrahydro-3α-methoxycarbonylfuro[3,4-b]furan-2,4-dione (0.512 g.) in dimethylformamide (10 ml., dried by distillation from calcium hydride) is added to a stirred suspension of sodium hydride (0.100 g.) in the same solvent (10 ml.) under an atmosphere of argon. 1-Iodopropane (2.5 ml.) is added and the mixture is heated for 3 hours at 80° C. After cooling to 20°–25° C., the mixture is added to a saturated aqueous solution of ammonium chloride (500 ml.) and extracted with chloroform (3 × 100 ml.). The combined extracts are dried (sodium sulphate) and evaporated to give as the residue, a C3-epimeric mixture of (±)-6α-n-butyl-3,3aα,6,6aα-tetrahydro-3-methoxycarbonyl-3N-propyl-furo[3,4-b]furan-2,4-dione. A solution of this residue in glacial acetic acid (18 ml.) and concentrated hydrochloric acid (18 ml.) is heated at 110°–120° C. for 2 hours. After cooling to 20°–25° C., the solution is evaporated. The residue obtained is dissolved in the minimum volume of methylene chloride and adsorbed by evaporation of solvent onto silica gel (2.5 g.), which has been deactivated with water (12% w/w) and equilibrated with a 1:33:66 v/v mixture (10% w/w) of acetone, chloroform and petrol respectively. The silica gel residue is added to the top of a dry column (45 × 2.5 cm.) of silica gel (650 g.) prepared as above, and the column eluted with the above three component solvent mixture. Fractions (25 ml.) are then collected and analysed by TLC using System B. The fractions containing material of $R_f$ 0.45 are combined and evaporated. The residue obtained is crystallised from a mixture of ether and petrol to give in 21% yield (±)-6α-n-butyl-3,3aα,6,6aα-tetrahydro-3α-n-propylfuro[3,4-b]furan-2,4-dione, m.p. 105°–106° C. By a similar treatment of the fractions containing material of $R_f$ 0.31, there is obtained in 38% yield (±)-6α-n-butyl-3,3aα,6,6aα-tetrahydro-3β-n-propylfuro[3,4-b]furan-2,4-dione, m.p. 104°–106° C.

Using a similar procedure to that described above, but starting from the corresponding (±)-6-substituted-3,3aα,6,6aα-tetrahydro-3-α-methoxycarbonylfuro[3,4-b]furan-2,4-dione and corresponding 1-iodo-alkane, there are obtained in situ the C3-epimeric mixtures of the following (±)-6-substituted-3,3aα,6,6aα-3-alkyl-3-methoxycarbonylfuro[3,4-b]furan-2,4-diones:

| Ester No. | 6-substituent | 3-alkyl substituent |
|---|---|---|
| 1 | α-n-butyl | n-pentyl |
| 2 | α-n-butyl | n-decyl |
| 3 | β-n-butyl | n-pentyl |
| 4 | β-n-butyl | n-decyl |
| 5 | α-n-butyl | methyl |
| 6 | β-phenyl | methyl | and, by hydrolysis and decarboxylation of the above 3-alkyl-3-methoxycarbonyl derivatives, the corresponding (±)-6-substituted-3,3aα,6,6aα-3-alkyl-furo[3,4-b]furan-2,4-diones:

| Compound No. | 6-substituent | 3-alkyl substituent | m.p.° C. | $R_f$ (system) | Yield % |
|---|---|---|---|---|---|
| 1 | α-n-butyl | α-n-pentyl | 129–130 | 0.59, B | 19 |
| 2 | α-n-butyl | β-n-pentyl | 121–123 | 0.35, B | 35 |
| 3 | α-n-butyl | β-n-decyl | 104–108 | 0.62, B | 17 |
| 4 | α-n-butyl | β-n-decyl | 105–110 | 0.42, B | 30 |
| 5 | β-n-butyl | α-n-pentyl | 129–130 | 0.40, B | 9 |
| 6 | β-n-butyl | β-n-pentyl | 132–147 | 0.30, B | 34 |
| 7 | β-n-butyl | β-n-decyl | 137–139 | 0.35, B | 36 |
| 8 | α-n-butyl | αmethyl | 75–76 | 0.70, A | 7 |
| 9 | α-n-butyl | β-methyl | 82–83 | 0.64, A | 30 |
| 10 | β-phenyl | α-methyl | 160–161 | 0.40, A | 6 |
| 11 | β-phenyl | β-methyl | 191–192 | 0.33, A | 58 |

Note 1:
Solvent mixtures used as dry column eluants and for equilibration of column silica gel for the purification of the compounds immediately above are as follows:-
Compounds No. 1–4; 1:33:66 v/v of acetone, chloroform and petrol respectively.
Compounds No. 5–6; 1:1 v/v of ether and petrol.
Compound No. 7; 1:33:66 v/v of acetone, chloroform and hexane respectively.
Note 2:
Compounds No. 8 and 9 are separated by high pressure liquid chromatography -continued

| Compound No. | 6-substituent | 3-alkyl substituent | m.p.° C. | R$_f$ (system) | Yield % |
|---|---|---|---|---|---|

(HPLC) on a similar column to that used in Example 14 using a 1:33:66 v/v mixture of acetone, chloroform and hexane respectively as eluant, and a flow rate of 4 ml./minute.

EXAMPLE 17

A solution of succinic anhydride (1.6 g.) in tetrahydrofuran (20 ml.) is stirred with a solution of α-dimethylsulphuranylidene-n-hexanophenone (4.0 g.) in tetrahydrofuran (20 ml.) for 2 hours at room temperature. The mixture is then heated under reflux for 5 hours and evaporated to dryness. The residual oil is dissolved in ethyl acetate (100 ml.) and the solution washed with a saturated aqueous solution of sodium hydrogen carbonate and then with water. The ethyl acetate solution is dried (magnesium sulphate) and evaporated. The residue obtained is dissolved in the minimum volume of methylene chloride and adsorbed, by evaporation of solvent, onto silica gel (10 g.) which has been deactivated with water (12% w/w) and equilibrated with a 3:2 v/v mixture of ether and hexane (10% w/w). The silica gel is added to the top of a dry column (45 × 2.5 cm.) of silica gel (650 g.) prepared as above, and the column eluted with the above mixture of ether and hexane. Fractions (25 ml.) are then collected and analysed by TLC (System B). The fractions (No. 58 to 76) containing material of R$_f$ 0.24 are combined and evaporated. The residue thus obtained is recrystallised from a mixture of acetone and petrol to give a C6-epimeric mixture of (±)-6-n-butyl-3,3aα,6,6aα,tetrahydro-6aα-phenylfuro[3,4-b]furan-2,4-dione (0.130 g.), m.p. 145° C.

The α-dimethylsulphuranylidene-n-hexanophenone used as starting material is obtained as follows:

Anhydrous aluminum chloride (0.120 g.) is added to an ice-cooled solution of n-hexanophenone (21.1 g.) in anhydrous ether (20 ml.). The mixture is stirred and ice-cooled to a temperature below 10° C. during the dropwise addition of bromine (6.0 ml.) during 1 hour. The mixture is evaporated and the residual oil dissolved in ether (100 ml.). The solution obtained is washed first with a saturated aqueous solution of sodium thiosulphate (3 × 30 ml.) and then with water. After drying (sodium sulphate) the ethereal solution is evaporated to give α-bromo-n-hexanophenone as an oil (28.0 g.) which is used without further purification.

A mixture of α-bromo-n-hexanophenone (25.2 g.), dimethyl sulphide (12.4 g.), silver tetrafluoroborate (19.4 g.) and acetone (60 ml.) is stirred at 20°–25° C. for 16 hours. The residual silver salts are separated by filtration and washed with ethanol (20 ml.). The filtrate and washings are then evaporated and the residual syrup is extracted with ether (3 × 200 ml.). Evaporation of the ethereal extracts gives 1-benzoylpentyl dimethylsulphonium tetrafluoroborate as a syrup (36.0 g.), which is used without further purification.

A mixture of a saturated aqueous solution (72 ml.) of potassium carbonate and a 12.5 M aqueous solution (10 ml.) of sodium hydroxide is added to an ice-cooled, vigorously stirred solution of 1-benzoylpentyl dimethylsulphonium tetrafluoroborate (36.0 g.) in chloroform (100 ml.) at such a rate that the temperature does not exceed 10° C. After the addition is complete, the mixture is allowed to warm up to 20° C. and is stirred at this temperature for 15 minutes. The mixture is then separated by filtration and the chloroform layer of the filtrate is dried (sodium sulphate) and evaporated to give an oily residue. Trituration of this residue with ether (5 ml.) gives crystalline α-dimethylsulphuranylidene-n-hexanophenone (4.0 g.), which is used as starting material immediately.

EXAMPLE 18

The process described in Example 4 is repeated except that (±)-6α-n-decyl-3,3aα,6,6aα-tetrahydro-3α-methoxycarbonylfuro[3,4-b]furan-2,4-dione is used as starting material. There is thus obtained (±)-6α-n-decyl-3,3aα,6,6aα-tetrahydrofuro[3,4-b]furan-2,4-dione in 80% yield, as a crystalline solid, m.p. 113°–114° C.

EXAMPLE 19

Using a similar procedure to that described in Example 16 for the preparation of (±)-6α-n-butyl-3,3aα,6,6aα-tetrahydro-3-n-propylfuro[3,4-b]furan-2,4-dione, there is obtained from (±)-6β-n-butyl-3,3aα,6,6aα-tetrahydro-3α-methoxycarbonylfuro[3,4-b]furan-2,4-dione, first the C3-epimeric mixture (±)-6β-n-butyl-3,3aα,6,6aα-tetrahydro-3-methyl-3-methoxycarbonylfuro[3,4-b]furan-2,4-dione in situ and then, after hydrolysis and decarboxylation using the procedure described in Example 16, the C3-epimeric mixture (±)-6β-n-butyl-3,3aα,6,6aα-tetrahydro-3-methylfuro[3,4-b]furan-2,4-dione. This mixture is separated by high pressure liquid chromatography (HPLC) on a similar column to that used in Example 14 but using a 40:9:1 v/v mixture of ether, petrol and acetone respectively as eluant, and a flow rate of 4 ml./minute. There is thus obtained in 10% yield from fractions (25 ml.) numbered 14–16, (±)-6β-n-butyl-3,3aα,6,6aα-tetrahydro-3α-methylfuro[3,4-b]furan-2,4-dione, m.p. 97° C., R$_f$ 0.76 (System A). Similarly from fractions numbered 18–24, there is obtained in 46% yield (±)-6β-n-butyl-3,3aα,6,6aα-tetrahydro-3β-methylfuro[3,4-b]furan-2,4-dione, m.p. 74–76° C., R$_f$ 0.68 (System A).

EXAMPLE 20

A mixture of 50 parts by weight of canadensolide, 27 parts by weight of lactose, and 20 parts by weight of maize starch is thoroughly stirred, and a paste formed from 2 parts by weight of maize starch and 40 parts by weight of water is added and thoroughly mixed. The resulting mass is passed through a 16-mesh screen, dried at 60° C. to constant weight and then passed through a 20-mesh screen. 1 Part by weight of magnesium stearate is added to the granules thus obtained and the mixture is compressed into tablets by conventional means. There are thus obtained tablets each weighing 100 ml. and containing 50 mg. of active ingredient which are suitable for oral administration to man for therapeutic purposes.

EXAMPLE 21

The process described in Example 20 is repeated except that 200 parts by weight of canadensolide, 120.5 parts by weight of lactose, 60 parts by weight of maize starch, a paste formed from 6 parts by weight of maize starch and 120 parts by weight of water, and 3.5 parts by weight of magnesium stearate are used as ingredients. There are thus obtained tablets each weighing 400 mg. and containing 200 mg. of active ingredient which are suitable for oral administration to man for therapeutic purposes.

EXAMPLE 22

A mixture of 50 parts by weight of canadensolide, 33 parts by weight of calcium phosphate, 10 parts by weight of microcrystalline cellulose and 4 parts by weight of calcium carboxymethylcellulose is thoroughly stirred and a paste formed from 2 parts by weight of polyvinylpyrrolidone and 40 parts by weight of water is added and thoroughly mixed. The resulting mass is passed through a 16-mesh screen, dried at 60° C. to constant weight and then passed through a 20-mesh screen. 1 Part by weight of magnesium stearate is added to the granules thus obtained and the mixture is compressed into tablets by conventional means. There are thus obtained tablets each weighing 100 mg. and containing 50 mg. of active ingredient which are suitable for oral administration to man for therapeutic purposes.

EXAMPLE 23

The process described in Example 22 is repeated except that 200 parts by weight of canadensolide, 120 parts by weight of calcium phosphate, 40 parts by weight of microcrystalline cellulose, 20 parts by weight of calcium carboxymethylcellulose, a paste formed from 16 parts by weight of polyvinylpyrrolidone and 320 parts by weight of water, and 4 parts by weight of magnesium stearate are used as ingredients. There are thus obtained tablets each weighing 400 mg. and containing 200 mg. of active ingredient which are suitable for oral administration to man for therapeutic purposes.

EXAMPLE 24

The canadensolide used as active ingredient in any one of Examples 20–23 may be replaced by a similar amount of 3-epi-dihydrocanadensolide (6β-n-butyl-3,3aα,6,6aα-tetrahydro-3β-methylfuro[3,4-b]furan-2,4-dione), or by any one of the known racemic compounds hereinbefore described.

EXAMPLE 25

The canadensolide used as active ingredient in any one of Examples 20–23 may be replaced by a novel compound as described in any one of Examples 1–8, or in a numbered part thereof.

EXAMPLE 26

The canadensolide used as active ingredient in any one of Examples 20–23 may be replaced by a novel compound as described in any one of Examples 9–19 or in a numbered part thereof.

What we claim is:

1. A 3,3a,6,6a-tetrahydrofuro[3,4-b]furan-2,4-dione of the formula:

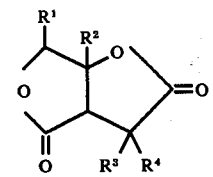

I wherein $R^1$ is hydrogen, an alkyl radical of from 1 to 10 carbon atoms or a phenyl radical; $R^2$ and $R^3$ are hydrogen; and $R^4$ is a radical of the formula $R^5SCH_2$ - wherein $R^5$ is a benzyl radical or a phenyl radical optionally bearing one or two substituents selected from halogen atoms, alkyl and alkoxy radicals each of from 1 to 4 carbon atoms, and carboxylic acid radicals.

2. A pharmaceutical composition for internal use for the treatment of gastric or duodenal ulcers which comprises as active ingredient an effective amount of a compound according to claim 1 and a pharmaceutically-acceptable carrier.

3. A composition as claimed in claim 2 which is in a form suitable for oral administration as a tablet, capsule, aqueous suspension, oily solution or suspension, emulsion, dispersible powder, granule, syrup or elixir.

4. A method for the treatment of duodenal or gastric ulcers in warm-blooded animals, which comprises administering to the said animal an effective amount of a composition as claimed in claim 1.

* * * * *